United States Patent [19]

Kent et al.

[11] Patent Number: 4,675,189
[45] Date of Patent: Jun. 23, 1987

[54] MICROENCAPSULATION OF WATER SOLUBLE ACTIVE POLYPEPTIDES

[75] Inventors: John S. Kent, Cupertino, Calif.; Danny H. Lewis, Birmingham, Ala.; Lynda M. Sanders, Palo Alto, Calif.; Thomas R. Tice, Birmingham, Ala.

[73] Assignee: Syntex (U.S.A.) Inc., Palo Alto, Calif.

[21] Appl. No.: 699,715

[22] Filed: Feb. 8, 1985

Related U.S. Application Data

[63] Continuation of Ser. No. 329,832, Dec. 11, 1981, which is a continuation-in-part of Ser. No. 207,864, Nov. 18, 1980, abandoned.

[51] Int. Cl.$^4$ .............................................. A61K 9/50
[52] U.S. Cl. .................................. 424/490; 424/426; 424/468; 424/462; 424/489; 424/497; 514/800; 514/963
[58] Field of Search ..................... 514/963, 800; 424/19-22, 426, 468, 462, 489, 490, 497

[56] References Cited

U.S. PATENT DOCUMENTS

| | | | |
|---|---|---|---|
| 3,773,919 | 11/1973 | Boswell et al. | 424/19 |
| 3,824,227 | 7/1984 | Rees et al. | 260/112.5 |
| 3,826,796 | 7/1974 | Sarantakis et al. | 260/112.5 |
| 3,835,108 | 9/1974 | Immer et al. | 260/112.5 |
| 3,853,837 | 12/1974 | Fujino et al. | 260/112.5 |
| 3,887,699 | 6/1975 | Yolles | 424/19 |
| 3,892,723 | 7/1975 | McKinley et al. | 260/112.5 |
| 3,896,105 | 7/1975 | Chai et al. | 260/112.5 |
| 3,972,859 | 8/1976 | Fujino et al. | 260/112.5 LH |
| 3,991,776 | 11/1976 | Schmitt et al. | 128/335.5 |
| 4,003,846 | 1/1977 | Kuhn et al. | 252/316 |
| 4,008,209 | 2/1977 | Fujino et al. | 260/112.5 LH |
| 4,010,125 | 3/1977 | Schally et al. | 260/8 |
| 4,010,196 | 3/1977 | Tsuk | 260/484 |
| 4,066,568 | 1/1978 | Nakazawa et al. | 252/316 |
| 4,076,798 | 2/1978 | Casey et al. | 424/22 |
| 4,093,709 | 6/1978 | Choi et al. | 424/19 |
| 4,107,071 | 8/1978 | Bayless | 252/316 |
| 4,131,648 | 12/1978 | Choi et al. | 424/22 |
| 4,166,800 | 9/1979 | Fong | 252/316 |
| 4,188,470 | 10/1978 | Casey et al. | 424/19 |
| 4,211,769 | 7/1980 | Okado et al. | 424/177 |
| 4,234,571 | 11/1980 | Nestor et al. | 424/177 |
| 4,293,539 | 10/1981 | Ludwig | 424/19 |
| 4,318,905 | 3/1982 | Nestor et al. | 424/177 |
| 4,341,767 | 7/1982 | Nestor et al. | 424/177 |
| 4,439,199 | 3/1979 | Amkraut et al. | 604/894 |
| 4,490,291 | 12/1981 | Fujino | 260/112.5 LH |
| 4,526,938 | 7/1985 | Churchill et al. | 525/415 |

FOREIGN PATENT DOCUMENTS

2026976  2/1980  United Kingdom .
2034182A  6/1980  United Kingdom .

OTHER PUBLICATIONS

*Encyclopedia of Chemical Technology*, vol. 13, 2nd Ed., Wiley, New York, 1967, pp. 436-456.
"Microencapsulation" by L. A. Luzzi, *J. Pharm. Sci.* 59, pp. 1367-1376 (1970).
"New Long-Acting Injectable Microcapsule Contraceptive System" by L. R. Beck et al., Am. J. Obstet. Gynecol., pp. 419-426, Oct. 1, 1979.
"Long-Acting Steroidal Contraceptive Systems" by L. R. Beck et al., *Res. Frontiers in Fertility Regulation*, Jul. 1980.
"Sustained Release of Antibiotics from Biodegradeable Microcapsule" by D. H. Lewis et al., 7th Intl. Symposium on Controlled Release of Bioactive Materials, Jul. 28-30th, 1980.
"Lactic/Glycolic Acid Polymers", by D. L. Wise, et al., in *Drug Carriers in Biology and Medicine* G. Gregoriadis ed., Academic Press, pp. 237-270, 1979.
"A New Long-Acting Injectable Microcapsule System for the Administration of Progesterone" by L. R. Beck et al., *Fertility and Sterility*, 31, pp. 545-551, 1979.
"Long-Acting Delivery Systems for Narcotic Antagonists II": S. Yolles, et al., *J. Pharm. Sci.*, 64, pp. 348-349, 1975.
"Degradation Rates of Oral Resorbable Implants (Polylactates and Polyglycolates): Rate Modification with Changes in PLA/PGA Copolymer Ratios" by R. A. Miller et al., *J. Biomed. Mater. Res.* 11, pp. 711-719, 1977.
"Sustained Delivery of a Narcotic Antagonist from Lactic/Glycolic Acid Copolymer Implants" by D. E. Wise et al., in *Polymeric Delivery Systems* Ed. by R. J. Kostelnik, 1978.
"Control Delivery Release of Macromolecules", Chemtech, pp. 98-105, Feb. 1982.
"Controlled Delivery of an LHRH Analogue from Biodegradable Injectable Microspheres" by L. M. Sanders et al., Journal of Controlled Release, vol. 2, pp. 187-195, 1985.
"An Injectable Biodegradable Controlled Release Delivery System for Nafarelin Acetate", by L. M. Sanders et al., in *LHRH and its Analogues*, Labrie, Belanger and Dupont Eds., pp. 53-62, 1984.
"Inhibition of Prostate Tumors by Agonistic and Antagonistic Analogs of LHRH", by A. V. Schally et al., *The Prostate*, vol. 4, pp. 545-552, 1983.
"Current Status of Antagonistic Analogs of LHRH as a Contraceptive Method in the Female" by A. V. Schally, et al., *Research Frontiers in Fertility*, vol. 2, No. 5, 1983.
"Long-Acting Delivery Systems for Peptides: Inhibition of Rat Prostate Tumors by Controlled Release of (D-Trp6)-Luteinizing Hormone-Releasing Hormone from Injectable Microcapsules" by A. V. Schally et al.,

*Primary Examiner*—Shep K. Rose
*Attorney, Agent, or Firm*—Ellen J. Wise; Tom M. Moran; Alan Krubiner

[57] ABSTRACT

This invention concerns novel sustained release microcapsule compositions comprising water-soluble, hormonally active polypeptides and, optionally, a polymer hydrolysis modifying agent encapsulated in a biocompatible, biodegradable polymer.

18 Claims, No Drawings

(List continued on next page.)

OTHER PUBLICATIONS

Proc. Natl. Acad. Sci. vol. 81, pp. 5845–5848, 1984.

"Prolonged Controlled Release of Nafarelin, a Luteinizing Hormone-Releasing Hormone Analogue, from Biodegradable Polymeric Implants: Influence of Composition and Molecular Weight of Polymer" by L. M. Sanders et al., *J. Pharm. Sci.*, 75, pp. 356–360, 1986.

"Radioimmunoassay of D-Trp6-LHRH: Its Application to Animal Pharmacokinetic Studies after Single Injection and Long-Acting Formulation Administration" by E. Exan, et al., *Regulatory Peptides* 14, pp. 155–167 (1960).

"Microencapsulation of the Peptide Nafareline Acetate for Controlled Release" by J. S. Kent, et al., Proceedings of an International Workshop on Long-Acting Contraceptive Delivery Systems, May 31–Jun. 3, 1983.

"Comparisons of the Potential Utility of LHRH Agonists and Antagonists for Fertility Control" by B. H. Vickery, *J. Steroid Biochem.*, 23, pp. 779–791 (1985).

*Microencapsulation*, edited by J. R. Nixon, published by Marcel Dekker, 1976, pp. 1–5.

*Biodegradable Semipermeable Microcapsules Capsules Containing Enzymes, Hormones, Vaccines and Other Biologicals*, T. M. S. Chang, *Journal of Bioengineering*, vol. 1, pp. 25–52 (1976).

*Microencapsulation of the Peptide Nafarelin Acetate for Controlled Release*, J. S. Kent et al., *Long Acting Contraceptive Delivery Systems*, Sttachni et al., pp. 169–179, (1984).

MICROENCAPSULATION OF WATER SOLUBLE ACTIVE POLYPEPTIDES

This is a continuation of application Ser. No. 329,832 filed Dec. 11, 1981, which is a continuation in part of application Ser. No. 207,864 filed Nov. 18, 1980, now abandoned.

BACKGROUND OF THE INVENTION

1. Field of the Invention

This invention relates to a microcapsule composition comprising a core containing at least one water-soluble, hormonally active polypeptide and optionally a polymer hydrolysis modifying agent encapsulated in a biodegradable, biocompatible copolymer excepient. These compositions have sustained release characteristics. More specifically it relates to microcapsules wherein the core contains water-soluble polypeptides which are luteinizing hormone-releasing hormones, or mammalian growth hormones or polypeptides having thymosin-like activity and optionally an organic acid or its salts, or an acidic, neutral or basic inorganic salt which is capable of modifying the hydrolysis rate of the polymer excipient, encapsulated by a biocompatible, biodegradable excipient. These microcapsules demonstrate a sustained release of drug over time, particularly when administered parenterally.

2. Related Art

There are several publications that disclose combinations of polymers and drugs designed to give sustained or delayed release of drugs. For example U.S. Pat. No. 3,773,919 discloses controlled drug release compositions in which the core comprises a drug encapsulated in polylactide/glycolide copolymers. See also U.S. Pat. No. 4,293,539 which relates to microencapsulated antibacterial compound formulations.

Microencapsulated compositions for sustained release of enzymes, hormones, vaccines, and other biologicals are mentioned in a paper by T. Chang, J. Bioeng., Vol 1, pp 25–32, 1976.

Polylactic acid polymers, polylactide/glycolide copolymers and polyglycolic acid polymers and related materials, for surgical elements and the like, incorporating a medicament and demonstrating slow release properties have been prepared. See for example U.S. Pat. Nos. 3,991,776; 4,118,470; 4,076,798.

SUMMARY OF THE INVENTION

This invention covers a pharmaceutical composition designed for sustained release of an effective amount of drug over an extended period of time prepared in microcapsule form wherein the composition comprises at least one hormonally active water-soluble polypeptide in an effective amount greater then a conventional single dose; optionally, at least one polymer hydrolysis modifying agent; and a biocompatible, biodegradable encapsulating polymer.

The hormonally active polypeptides may be a luteinizing hormone-releasing hormone (LH-RH) polypeptide or analogues thereof which affect fertility and physiological effects related thereto, mammalian growth hormones which affect growth or low molecular weight polypeptides having thymosin-like activity which affect immunological competence.

One or more polymer hydrolysis modifying agents may optionally be present in these compositions. These agents, when present, may decrease or increase the rate of polymer hydrolysis. They are low molecular weight non-toxic organic acids or acidic, neutral or basic inorganic salts.

The encapsulating material may be a synthetic polymer comprising either poly(o-hydroxycarboxylic acids), poly(lactones), poly(acetals), poly(orthoesters) or poly(orthocarbonates).

The process for preparing these compositions is also disclosed, which process involves phase-separation techniques whereby the encapsulating polymer is precipitated onto water droplets containing the peptide and hydrolysis modifying agent, dispersed as an water-in-oil emulsion, by the addition of a coacervation agent which is a non-solvent for the encapsulating polymer. The capsules are then hardened, washed and dried.

DETAILED DESCRIPTION OF THE INVENTION

Hormonally active polypeptides are those peptides which have a specific regulatory effect on the activity of a certain body organ. Generally they are secreted by an endocrine gland. Some peptides not secreted by an endorine gland, however, exhibit a specific regulatory affect on a body organ and therefore are also classifiied as hormonally active compounds. Synthetically prepared analogues of naturally occuring hormonally active polypeptides are to be considered as falling within the scope of this definition. Pharmaceutically acceptable salts of the naturally occuring hormones and their synthetic analogues which retain the same type of activity as their parent also are to be considered within the scope of this invention.

Hormonally active peptides comprise a diverse group of proteins but because of their functional specificity, they can conveniently be grouped into discrete classifications by physiological effect. Each protein group generally regulates one specific physiological function by interacting only with the organ or organs directly affecting that function. For example LH-RH-active polypeptides act on the anterior pituitary gland to effect release of hormones which affect the activity of reproductive organs. Growth hormones act on the liver causing it to release somatomedin, the peptide factor responsible for skeletal growth. Thymosin and thymically active peptides interact with the autoimmune system, enhancing the ability of the body's immune system to combat disease.

With regard to specific hormonally active polypeptides of interest herein, in a first instance there is the naturally occuring luteinizing hormone-releasing hormone (LH-RH) polypeptide and synthetic analogues thereof The naturally occuring LH-RH peptide is produced in the hypothalmic region of the brain and controls the reproductive cycle of mammals by acting on the anterior pituitary gland to effect release of luteinizing homone (LH) and follicular stimulating hormone (FSH) which in turn act on the gonads to stimulate the synthesis of steroid hormones and to stimulate gamete maturation. The pulsatile release of LH-RH thereby controls the reproductive cycle in mammals. Additionally, LH-RH has effects in the placenta, in releasing HCG, and directly on the gonads.

Agonist analogues of LH-RH are useful for the control of fertility by two mechanisms of action. Low doses of LH-RH analogues can stimulate ovulation and are useful in the treatment of hypothalmic and ovulatory infertility. Additionally they can be used for hypogonadal conditions and impotence, and to stimulate spermatogenesis and androgen production in the male.

Paradoxically, larger doses of highly potent and long-lasting analogues of LH-RH have an opposite effect and block ovulation in the female and suppress spermatogenesis in the male. Related to these effects is a suppression of normal circulating levels of sexual steroids of gonadal origin, including reduction in accessory organ weight in the male and female. In domestic animals this paradoxical effect promotes weight gain in a feed-lot situation, stimulates abortion in pregnant animals and in general, acts as a chemical sterilant. A full list of the paradoxical high dose effects is set out in U.S. Pat. No. 4,234,571.

There is also the group of LH-RH analogues termed antagonists. These polypeptides have the paradoxical effect shown by LH-RH agonists but at low dose levels relative to naturally occuring LH-RH. Such compounds are to be included within the scope of this invention.

The natural LH-RH peptide is a decapeptide comprised of naturally occuring amino acids (which have the L-configuration except for the achiral amino acid glycine). Its sequence is as follows: (pyro)Glu-His-Trp-Ser-Tyr-Gly-Leu-Arg-Pro-Gly-NH$_2$. Many analogues of this natural material have been studied. The benificial effectiveness of these analogues has been varied. The most significant modification where agonists are concerned is obtained by changing the 6-position residue from Gly to a D-amino acid, for example, D-Ala, D-Leu, D-Phe or D-Trp. Antagonist activity can be best realized by substituting the naturally occuring 2-position His amino acid residue with with a D-amino acid residue. These analogues show increased activity relative to LH-RH.

In addition to modifications at position 6, increased agonist activity may be obtained by the following modifications: modifying position 10 to afford a nonapeptide as an alkyl-, cycloalkyl- or fluoroalkylamine, or by replacing Gly-NH$_2$ by an α-azaglycine amide; substituting N-methyl-leucine for leucine in position 7; replacing tryptophan in position 3 by 3-(1-naphthyl)-L-alanine; substituting the position 5 tyrosine residue with phenylalanine or 3-(1-pentafluorophenyl)-L-alanine; and the subsititution at position 6 of unnatural D-amino acid residues containing two or more carbocyclic (or perhydroaryl) rings or a phenyl (or cyclohexyl) ring which is highly alkyl substituted. These specific compounds represent some of the more useful fertility affecting LH-RH type polypeptides which have been developed to date. This is not intended to be an exhaustive or exclusive list of all LH-RH active polypeptides which have been made or which can or may be made. They are simply set out to illustrate the type of compounds which are the subject of this invention. Any or all of them can be interchangeably substituted into the compositions of this invention.

The LH-RH compounds of most interest herein are those from the last mentioned group wherein the 6-position of the naturally occuring LH-RH material is replaced with a specific non-natural D-amino residue containing lipophilic carbocyclic residues, particularly residues containing two or more highly alkyl substituted carbocyclic aryl (or perhydroaryl) rings or a phenyl (or cyclohexyl) ring. These particular polypeptides are the subject of U.S. patent application Ser.No. 47,661, filed June 11, 1979 now U.S. Pat. No. 4,234,571, and are prepared in accordance with the procedures set forth therein. That patent is incorporated in full herein by reference and made a part of this application. Reference is made to that patent for a full description of the synthetic nonapeptides and decapeptides of most interest herein. A full description of the formulas, nomenclature and synthetic methods for preparing these compounds are found therein. The compounds set out therein comprise the preferred embodiment of synthetic LH-RH analogues for incorporation into microcapsule formulations in this invention.

More specifically the LH-RH polypeptides of most interest in this invention are the nonapeptides and decapeptides of the formula:

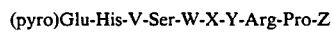

and the pharmaceutically acceptable salts thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue

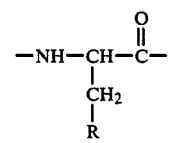

wherein R is (a) a carbocyclic aryl-containing radical selected from the group consisting of naphthyl, anthryl, fluorenyl, phenanthryl, biphenyl, benzhydryl and phenyl substituted with three or more straight chain lower alkyl groups; or (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, Isoluecyl, nor-leucyl or N-methl-leucyl;

Z is glycinamide or —NH—R$_1$, wherein

R$_1$ is lower alkyl, cycloalkyl, fluoro lower alkyl or

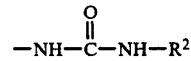

R$_2$ is hydrogen or lower alkyl.

The preferred LH-RH-active synthetic nona and decapeptides of this invention are those wherein X is 3-(2-naphthyl)-D-alanyl or 3-(2,4,6-trimethylphenyl)-D-alanyl; Z is glycinamine; V is tryptophyl or phenylalanyl; W is tyrosyl and Y is leucyl or N-methyl-leucyl.

The most preferred coumpound in application Ser. No. 47,661 and herein for LH-RH synthetic analogues are:

(pyro)Glu-His-Trp-Ser-Tyr-3-(2-naphthyl)-D-alanyl-Leu-Arg-Pro-Gly-NH$_2$, (pyro)Glu-His-Trp-Ser-Tyr-3-(2-naphthyl)-D-alanyl-n-methyl-Leu-Arg-Pro-Gly-NH$_2$, (pyro)Glu-His-Phe-Ser-Tyr-3-(2-naphthyl)-D-alanyl-Leu-Arg-Pro-Gly-NH$_2$, (pyro)Glu-His-Trp-Ser-Tyr-3-(2,4,6-trimethylphenyl)-D-alanyl-Leu-Arg-Pro-Gly-NH$_2$, (pyro)Glu-His-Trp-Ser-Tyr-3-(2-naphtyl)-D-alanyl-Leu-Arg-Pro-NHEt, being comprised of the following number and sequence of amino acids.

| HUMAN GROWTH HORMONE | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | 5 | | | | | 10 | | | | | 15 | | | | | 20 | | | | | 25 | | | | | 30 | |
| 1 | F | P | T | I | P | L | S | R | L | F | D | N | A | M | L | R | A | H | R | L | H | Q | L | A | F | D | T | Y | Q | E |
| 31 | F | E | E | A | Y | I | P | K | E | Q | K | Y | S | F | L | Q | N | P | Q | T | S | L | C | F | S | E | S | I | P | T |
| 61 | P | S | N | R | E | E | T | Q | Q | K | S | N | L | Q | L | L | R | I | S | L | L | L | I | Q | S | W | L | E | P | V |
| 91 | Q | F | L | R | S | V | F | A | N | S | L | V | Y | G | A | S | N | S | D | V | Y | D | L | L | K | D | L | E | E | G |
| 121 | I | Q | T | L | M | G | R | L | E | D | G | S | P | R | T | G | Q | I | F | K | Q | T | Y | S | K | F | D | T | N | S |
| 151 | H | N | D | D | A | L | L | K | N | Y | G | L | L | Y | C | F | R | K | D | M | D | K | V | E | T | F | L | R | I | V |
| 181 | Q | C | R | S | V | E | G | S | C | G | F | | | | | | | | | | | | | | | | | | | |

| COMPOSITION | | | | | | | | | | | | | | |
|---|---|---|---|---|---|---|---|---|---|---|---|---|---|---|
| | 7 | ALA | A | | 14 | GLN | Q | | 26 | LEU | L | | 18 | SER | S |
| | 11 | ARG | R | | 13 | GLU | E | | 9 | LYS | K | | 10 | THR | T |
| | 9 | ASN | N | | 8 | GLY | G | | 3 | MET | M | | 1 | TRP | W |
| | 11 | ASP | D | | 3 | HIS | H | | 13 | PHE | F | | 8 | TYR | Y |
| | 4 | CYS | C | | 8 | ILE | I | | 8 | PRO | P | | 7 | VAL | V |

MOL. WT. = 22,128
NUMBER OF RESIDUES = 191

(pyro)Glu-His-Trp-Ser-Tyr-3-(2-naphtyl)-D-alanyl-N-methyl-Leu-Arg-Pro-NHEt, and their pharmaceutically acceptable salts.

Especially preferred is (pyro)Glu-His-Trp-Ser-Tyr-3-(2-naphthyl)-D-alanyl-Leu-Arg-Pro-Gly-NH$_2$ and its pharmaceutically acceptable salts.

A second group of hormonally active polypeptides of interest herein are mammalian growth hormones. Growth hormones may be considered generally any substance which stimulates growth. But the compounds of interest herein are those polypeptides secreted by the anterior pituitary gland which exerts an influence on protein, carbohydrate and lipid metabolism and controls the rate of skeletal and visceral growth. Generally, growth hormones are species specific polypeptides with molecular weights falling between 22,000 and 24,000 daltons. In several species, for example, humans and cattle, the growth hormone also possesses some of the activities of lactogenic hormones.

Human Growth Hormone (hGH) has been isolated, crystallized and characterized as a homogenous protein containing 191 amino acid residues and having a molecular weight of 22,128 daltons. It is may be isolated from humans alone or with a much larger molecule which is probably an association of the primary polypeptide with another as yet unspecified protein. There are at least 4 isohormones of the primary molecule.

The exact amino acid content and sequence of hGH has undergone some revisions since the initial sequencing was carried out. At present hGH is described as Two disulfide bridges are present in this molecule, one linking residues 67 and 165 and a second linking residues 182 and 189. The amino acid sequence given above is also set out in the *Atlas of Protein Sequence and Structure,* Vol 5, Suppl. 3, p. S-50, Dayhoff, M. O., Schwartz, R. M., and Orcutt, B. C., (Dayoff, M.O. ed) (1973) National Biomedical Research Foundation, Washington, D.C. .

A subsequent publication, by Martial, J. A., et al, in *Science,* 205:602-607 1979, sets out the complementary DNA nucleotide sequence for hGH. This DNA sequence predicts glutamine, asparagine, glutamine, glutamic acid, glutamine, aspartic acid, asparagine, and glutamine at positions 29, 47, 49, 74, 91, 107, 109 and 122 respectively, while degradative protein sequencing indicates glutamic acid, aspartic acid, glutamic acid, glutamine, glutamic acid, asparagine, aspartic acid, and glutamic acid at these positions.

Availability of hGH has until recently been limited to that which could be extracted from the pituitary gland of human cadavers. However, recombinant DNA techniques have made it possible recently to produce from bacteria biologically active hGH in relatively substantial quantities. See, for example, Martial, J. A. Baxter, J. D. and Hallewell, R. A., *Science,* 205:602-607, 1979.

Bovine Growth Hormone (bGH) has the same number of residues as hGH, 191, but there exists some differences in the amino acid residue sequence and in the numbers of particular residues. As set out in the *Atlas of Protein Sequence and Structure* identified above, bGH is comprised of the following sequence or amino acid residues:

| BOVINE GROWTH HORMONE | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | 5 | | | | | 10 | | | | | 15 | | | | | 20 | | | | | 25 | | | | | 30 | |
| 1 | A | F | P | A | M | S | L | S | G | L | F | A | N | A | V | L | R | A | Q | H | L | H | Q | L | A | A | D | T | F | K |
| 31 | E | F | E | R | T | Y | I | P | E | G | Q | R | Y | S | I | Q | N | T | Q | V | A | F | C | F | S | E | T | I | P | A |
| 61 | P | T | G | K | N | E | A | Q | Q | K | S | D | L | E | L | L | R | I | S | L | L | L | I | Q | S | W | L | G | P | L |
| 91 | Q | F | L | S | R | V | F | T | N | S | L | V | F | G | T | S | D | R | V | Y | E | K | L | K | D | L | E | E | G | I |
| 121 | L | A | L | M | R | E | L | E | D | G | T | P | R | A | G | Q | I | L | K | Q | T | Y | D | K | F | D | T | N | M | R |
| 151 | S | D | D | A | L | L | K | N | Y | G | L | L | S | C | F | R | K | D | L | H | K | T | E | T | Y | L | R | V | M | K |
| 181 | C | R | R | F | G | E | A | S | C | A | R | | | | | | | | | | | | | | | | | | | |

| COMPOSITION | | | | | | | | | | | | | | |
|---|---|---|---|---|---|---|---|---|---|---|---|---|---|---|
| | 15 | ALA | A | | 11 | GLN | Q | | 27 | LEU | L | | 13 | SER | S |
| | 13 | ARG | R | | 13 | GLU | E | | 11 | LYS | K | | 12 | THR | T |
| | 6 | ASN | N | | 10 | GLY | G | | 4 | MET | M | | 1 | TRP | W |
| | 10 | ASP | D | | 3 | HIS | H | | 13 | PHE | F | | 6 | TYR | Y |

-continued

| 4 CYS | C | 7 ILE | I | 6 PRO | P | 6 VAL | V |
|---|---|---|---|---|---|---|---|

MOL. WT. = 21,816
NUMBER OF RESIDUES = 191

Molecular cloning of DNA complementary to bGH mRNA by Miller, W. L., Martial, J. A., Baster, J. D., *J. of Biol. Chem.*, Vol. 255, No. 16, pp 7521–7524 (1980) confirms this sequence except at positions 47 and 66 where aspartic acid and glutamic acid are replaced by their respective amides.

The primary source of bGH is the pituitary glands of slaughtered cattle. Methods of obtaining such materials are known in the art, for example, see the W. L. Miller reference given above.

In addition this invention is to encompass the growth hormones of sheep and horses. The amino acid residue sequence of both these hormones has been reported in the *Atlas of Protein Sequence and Structure* as follows:

been shown that a fraction of blood, specifically, human serum prealbumin, also possesses such activity (U.S. Pat. No. 4,046,887).

The structure of the human serum prealbumin is now clearly established. It is a tetramer of the sub units, each which contains 127 amino acids in the same known sequence (KAUNDA Y. et al *J. BIOL CHEM.* 249:6796 (1974)); and even the 3-dimensional configuration has been determined (BLAKE, C. L. F. et al., *J. MOL BIOL.*, 121 (3): 339 19(1978). It has been found that deca-, undeca-, dodeca-, and tridecapeptides which represent the N-terminal sequence in human serum prealbumin subunits are extremely potent in increasing immunological competence in mammals. Further, mod-

| SHEEP GROWTH HORMONE | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | 5 | | | | | 10 | | | | | 15 | | | | | 20 | | | | | 25 | | | | | 30 | |
| 1 | A | F | P | A | M | S | L | S | G | L | F | A | N | A | V | L | R | A | Q | H | L | H | Q | L | A | A | D | T | F | K |
| 31 | E | F | E | R | T | Y | I | P | E | G | Q | R | Y | S | I | Q | N | T | Q | V | A | F | C | F | S | E | T | I | P | A |
| 61 | P | T | G | K | N | E | A | Q | Q | K | S | D | L | E | L | L | R | I | S | L | L | L | I | Q | S | W | L | G | P | L |
| 91 | Q | F | L | S | R | V | F | T | D | S | L | V | F | G | T | S | D | R | V | Y | E | K | L | K | D | L | E | E | G | I |
| 121 | L | A | L | M | R | E | L | E | D | V | T | P | R | A | G | Q | I | L | K | Q | T | Y | D | K | F | D | T | N | M | R |
| 151 | S | D | D | A | L | L | K | N | Y | G | L | L | S | C | F | R | K | D | L | H | K | T | E | T | Y | L | R | V | M | K |
| 181 | C | R | R | F | G | E | A | S | C | A | F | | | | | | | | | | | | | | | | | | | |

| COMPOSITION | | | | | | | |
|---|---|---|---|---|---|---|---|
| 115 ALA | A | 11 GLN | Q | 27 LEU | L | 13 SER | S |
| 13 ARG | R | 13 GLU | E | 11 LYS | K | 12 THR | T |
| 5 ASN | N | 9 Gly | G | 4 MET | M | 1 TRP | W |
| 11 ASP | D | 3 HIS | H | 13 PHE | F | 6 TYR | Y |
| 4 CYS | C | 7 ILE | I | 6 PRO | P | 7 VAL | V |

MOL. WT. = 21,859
NUMBER OF RESIDUES = 191

| HORSE GROWTH HORMONE | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | 5 | | | | | 10 | | | | | 15 | | | | | 20 | | | | | 25 | | | | | 30 | |
| 1 | F | P | A | M | P | L | S | S | L | F | A | N | A | V | L | R | A | Q | H | L | H | Q | L | A | A | D | T | Y | K | E |
| 31 | F | E | R | A | Y | I | P | E | G | Q | R | Y | S | I | Q | N | A | Q | A | A | F | C | F | S | E | T | I | P | A | P |
| 61 | T | G | K | D | E | A | Q | Q | R | S | D | M | E | L | L | R | F | S | L | L | L | I | Q | S | W | L | G | P | V | Q |
| 91 | L | L | S | R | V | F | T | N | S | L | V | F | G | T | S | D | R | V | Y | E | K | L | R | D | L | E | E | G | I | Q |
| 121 | A | L | M | R | E | L | E | D | G | S | P | R | A | G | Q | I | L | K | Q | T | Y | D | K | F | D | T | N | L | R | S |
| 151 | D | D | A | L | L | K | N | Y | G | L | L | S | C | F | K | K | D | L | H | K | A | E | T | Y | L | R | V | M | K | C |
| 181 | R | R | F | V | E | S | S | C | A | F | | | | | | | | | | | | | | | | | | | | |

| COMPOSITION | | | | | | | |
|---|---|---|---|---|---|---|---|
| 17 ALA | A | 12 GLN | Q | 26 LEU | L | 15 SER | S |
| 14 ARG | R | 13 GLU | E | 10 LYS | K | 8 THR | T |
| 5 ASN | N | 8 GLY | G | 4 MET | M | 1 TRP | W |
| 11 ASP | D | 3 HIS | H | 12 PHE | F | 7 TYR | Y |
| 4 CYS | C | 6 ILE | I | 7 PRO | P | 7 VAL | V |

MOL. WT. = 21,757
NUMBER OF RESIDUES = 190

These two growth hormones are presently available from the pituitary gland of the respective animals and are obtained by methods known in the art as set out for example in W. L. Miller reference given above.

Further of interest herein are short-chain peptides of 10–13 amino acids which demonstrate thymic activity. A number of substances are known which, when administered to animals, enhance the ability of an organism's immune system to combat disease. Among these substances are crude extracts of mycobacteria, glycopeptides and modification of glycpeptides which are derived therefrom, and "thymosins," a family of hormones secreted by a thymosin gland. Recently, it has ification of the amino acid sequence of these peptides at one or more positions by substituting another aminoacyl residue for that normally present, results in a set of peptides with a similar or enhanced activity. These peptides may be used clinically for human treatment in situations where immunologic competence is believed to be an important factor, for example, autoimmune diseases, (e.g., lupas, erythematosus, ulcerative colitis, autoimmune hemolytic anemia, thyrotoxicosis, rheumatoid arthritis, hepatic circhosis, thymic aplasia and dysplasis, augmentation of immunity of infection (e.g., bacterial, viral and fungal) disorders, Hodgkin's disease, hypogammaglobulinemic syndrome, aberrant cell proliferative conditions, decrease in immunological competence due to temperal decline in thymic hormone production, in chemical or radiologially induced immunosuppressed states, and so forth.

Peptides having thymic activity and which are of interest in this invention can be represented by the formula:

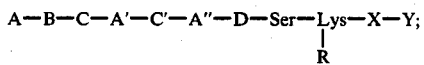

wherein:

A, A' and A" are each independently Gly, D-Ala, D-Leu, or D-Trp; wherein A may optionally be N-alkylated or N-acylated;

B is Pro, $\Delta^3$-Pro, Thz, or diMeThz;

C and C' are each independently Thr, Ser, Val, or alloThr;

D is Glu, Gln, Asp, or Asn;

R is hydrogen or lower alkyl or lower acyl, substituted for one of the hydrogens on the $\epsilon$-amino group of the lysyl residue;

X is Cys; Ala, ABU, or Cys(Me); and

Y is selected from the group consisting of hydroxy, Pro, Pro-Leu, and Pro-Leu-Met, —NH$_2$, ProNH$_2$, Pro-LeuNH$_2$ and Pro-leu-MetNH$_2$; and to the pharmaceutically acceptable salts thereof. Specifically, these peptides are decapeptides of the formula:

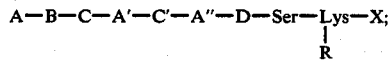

undecapeptides of the formula,

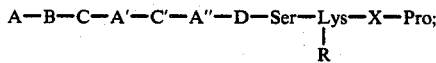

dodecapeptides of the formula,

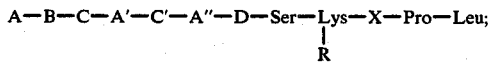

and tridecapeptides of the formula,

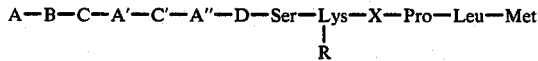

wherein A, A', A"; B; C and C'; D; R; and X are as defined above.

These synthetic peptides all demonstrate thymic activity. They are fully discussed and set out in U.S. patent application Ser.No. 218,886, filed Dec. 22, 1980. A full description of the nomenclature, synthetic methods, test procedures, a general and specific disclosure of the various synthetic peptides covered, a recitation of pharmaceutically acceptable salts for these peptides and various other materials necessary for a full and complete understanding of the scope of these peptides may be found there. That application is incorporated in full herein by reference and made a part hereof.

A set of preferred embodiments of the thymosin-like decapeptides, undecapeptides, dodecapeptides, and tridecapeptides of this invention is that wherein A, A' and A" are each independently Gly, D-Leu, D-Trp or D-Ala, wherein A may optionally be alkylated or acylated at the $\alpha$-amino group; B is Pro, C and C' are Thr; R is hydrogen, D is Glu, Gln, Asp or Asn; and X is Ala, Cys, or Cys(Me).

Especially preferred among these are those embodiments wherein A, A' and A" are each independently Gly or D-ala and wherein A may optionally be alkylated or acylated at the $\alpha$-amino group; D is Glu or Gln and X is Ala or Cys.

Another preferred set of embodiments is that wherein Y is —OH, —NH$_2$, Pro, or ProNH$_2$.

As set forth above and for convenience in describing these compounds, the conventional abbreviation for the various amino acids are used as generally accepted in the peptide art as recommended by the IUPAC-IUB Commission on Biochemical Nomenclature, Biochemistry, 11, 1726 (1972) and represent the L-amino acids. All peptide sequences mentioned herein are written according to the generally accepted convention whereby the N-terminal amino acid is on the left and the C-terminal amino acid is on the right.

The compositions of this invention will contain individually the hormonally active polypeptides in varying amounts depending upon the effect desired. For example, treatment of infertility with synthetic LH-RH peptides requires a low level of drug, while prevention of fertility and related effects requires a large dose relative to the activity of naturally occuring LH-RH.

For the LH-RH agonist fertility control it is expedient to prepare microcapsules which will release the drug at such a rate that the subject will receive between about 0.01 and 100 $\mu$g/kg body weight per day, preferably between 0.1 and 5.0 $\mu$g/kg body weight per day.

Human growth hormone quantities necessary to effect normal growth has not been precisely defined at this point. HGH administered in amounts of about 0.1 to 10.0 units per day based on body weight will effect increased linear growth in hGH deficient children. A recent study by D. Rudman, et al, *J. Clin. Endocrine Metabolism*, 49: 92–99, 1979 has demonstrated the onset of increased linear growth in children known to be deficient in hGH and showing shorter stature and lower than average growth rates for their age groups by the administration of 0.3 to 3.0 units of hGH per day.

Bovine, sheep or horse growth hormone may be administered on a daily basis in an amount anywhere between 5–100 mg/day. The dose may vary depending upon the activity of the growth hormone, the species, and the size of the animal.

Thymic peptides will be administered in the range of from about 10 ng/kg/day to about 20 mg/kg/day, preferrably from about 100 ng/kg/day to about 5 mg/kg/day. Expressed in alternative terms for an average (70 kg) adult human subject, this would be from 700 mg/day to 1.4 g/day, preferrably from 7 mg/day to 350 mg/day.

The compositions of this invention are formulated to contain the polypeptide in an amount which may vary between 0.01 and 40.0 weight % of the polymer used for encapsulation. Preferably the peptide will be present in the amount between 0.1 to 10.0 weight %.

The amount of peptide placed in a particular formulation depends not only on the desired daily dose but also on the number of days that dose level is to be maintained. While this amount can be calculated empirically, the actual dose delivered is a function of the degradation characteristics of the encapsulating polymer. Therefore the % weight of drug stated represent amounts which, when taken in conjunction with a particular polymer provide the desired release profile.

Optionally, certain chemicals which affect the rate of polymer hydrolysis may be dissolved in the aqueous solution containing the polypeptide before it is encapsulated by the polymer excipient. These chemicals are called polymer hydrolysis modifying agents. When present, these compounds may increase or decrease the rate at which the drug is released from the microcapsules. This effect is independent of a particular polymer composition or microcapsule size.

Four types of chemicals may be used to realize this effect, for example, organic acids and their salts, or acidic, neutral or basic inorganic salts. Low molecular weight carboxylic acids such as acetic acid, tartaric acid, citric acid, gluconic acid, oxalic acid, ascorbic acid, succinic acid, their non-toxic salts, and the like may be used. Inorganic acidic salts may be, for example, ammonium sulfate, ammonium chloride, ammonium nitrate, sodium bisulphate and the like. Inorganic neutral salts effective herein include metal halides such as, for example, sodium chloride, potassium chloride, sodium bromide, potassuim bromide, calcium chloride, magnesium chloride and the like. Inorganic basic salts include such salts as sodium carbonate, potassuim carbonate, trisodium phosphate, tripotassium phosphate and the like. Of these compounds it is most preferred to use either citric acid, sodium chloride or sodium carbonate. Combinations of these compounds will achieve the desired affect but the compositions described herein contain only one of these agents in a particular composition.

When present, the hydrolysis modifying agent will be added in an amount between 0.1 and 20% by weight of the polymer but preferably it will be present in the amount of 5 to 10%.

The number and type of encapsulating excipients which may be effectively used to practice this invention is limited only by the requirements that the material be biocompatible and biodegradable. That is, the polymer must be non-toxic to the host and must be of such composition that it is degradable by the body into metabolic products that have no deleterious or untoward effects on the body. These polymers must also be capable of forming microcapsules containing water-soluble drugs.

A number of polymers have been developed which meet these criteria. Various combinations of alpha hydroxycarboxylic acids and certain lactones can be condensed to form such polymers, particularly lactic acid and glycolic acid or combinations thereof. See, for example U.S. Pat. No. 3,773,919. Similiar biocompatible polymers based on glycolic acid and glycerol and the like also are known. See U.S. Pat. Nos. 3,991,776; 4,076,779 and 4,118,470 for examples of such compositions. Several new biocompatible, biodegradable polymers derived from polyorthoesters and polyorthocarbonates also may be effectively used as encapsulating excipients in the practice of this invention. These latter polymers are described in U.S. Pat. Nos. 4,093,709 and 4,138,344. There are also known polyacetals and polyorthoesters useful for this purpose as described in Polymer Letters 18, 293 (1980). This list is not intended to be exhaustive of the polymers which are compatible with the scope and intention of this invention but merely sets out examples to illustrate the type of polymeric excipients which may be used.

One preferred group of polymer excipients are the orthoester and orthocarbonate polymers having a repeating mer comprising a hydrocarbon radical and a symmetrical dioxycarbon unit of the general formula:

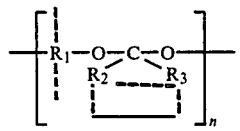

wherein $R_1$ is a multivalent hydrocarbon radical, $R_2$ and $R_3$ are hydrocarbon radicals with at least one of $R_2$ or $R_3$ bonded to the dioxycarbon through the oxygen linkage, and which polymers are synthesized by reacting a polyol with an orthoester or orthocarbonate. A full and complete description of the exact compositions, preparation, and properties of these polymers can be found in U.S. Pat. Nos. 4,093,709 and 4,138,344, which are incorporated by reference as if fully set out herein.

Also preferred are those polymers based on the condensation of divinyl ethers and polyols. These compounds are prepared by reacting polyol with a diketene acetal to form the polyacetal. A more detailed description and discussion of these polymers can be found in the journal, Polymer Letters, J. Heller, et al, 18, 293 (1980), which is incorporated herein by reference. Of similiar interest are those polyorthoesters prepared by a modification of the synthesis used to prepare the above polyacetals. These polymers are comprised of diketene acetal-diol condensates. For example, the diketene acetal 3,9-bis-(methylene)-2,4,8,10-tetraaoxaspiro[5,5]undecane can be condensed with 1,6-hexanediol to give a polyorthoester polymer which has degradation properties in vivo which make its use in the compositions of this invention desirable. Further preparation techniques and polymer characteristics for these compounds can be found in U.S. Pat. Nos. 4,093,709; 4,131,648; 4,138,344; and 4,180,646 all of which are incorporated herein by reference.

Most preferred herein are those polymers derived from the condensation of alpha hydroxycarboxylic acids and related lactones. The most preferred polymer excipients herein are derived from an alpha hydroxy acid, particularly lactic acid, glycolic acid or a mixture of the two.

The alpha hydroxy acid units from which the preferred excipients are prepared may be the optically active (D- and L-) forms or optically inactive (DL-, racemic) forms. For example, lactic acid, whether it is the principle polymer component or the comonomer component, can be present as D-lactic acid, L-lactic acid or DL-lactic acid.

Other comonomers, for example certain C3 to C18 carboxylic acids and certain lactones, can be used in the preparation of preferred polymers. Illustrative of such compounds are 3-propiolactone, tetramethylglycolide, b-butyrolactone, 4-butyrolactone, pivalolactone, and intermolecular cyclid esters of α-hydroxy butyric acid, α-hydroxyisobutyric acid, α-hydroxyvaleric acid, α-hydroxyisovaleric acid, α-hydroxy caproic acid, α-hydroxy-α-ethylbutyric acid,, α-hydroxyisopcaproic acid, α-hydroxy-3-methylvaleric acid, α-hydroxyheptanoic acid, α-hydroxyoctanoic acid, α-hydroxydecanoic acid, α-hydroxymysristic acid, α-hydroxystearic acid, and α-hydroxylignoceric acid.

Any of these compounds may be used as a comonomer in the preparation of acceptable polymers 3-butyrolactone can be used as the sole monomer or as the principle monomer along with any of the comonomers recited above. However it is most preferred to use lactic acid as the sole monomer or lactic acid as the principle monomer with glycolic acid as the comonomer.

The term polylactide is used to designate the general class of polymers which can be prepared from one or more of the preferred monomers listed above and includes those instances where a single alpha hydroxy acid or lactone is the only monomer in the polymer. For the most preferred polymers, those wherein the excipients are prepared solely from the lactic acid monomer or where lactic acid is the principle monomer and glycolic acid is the comonomer are termed poly(lactide-co-glycolide) copolymers.

The combinations of prefered monomer and comonomer which can be prepared are numerous but the most effective excipients are those polymers prepared from lactic acid alone or lactic acid and glycolic acid wherein the glycolic acid is present as a comonomer in a molar ratio of 100:0 to 40:60. It is most preferred to use a poly(lactide-co-glycolide) copolymer having a molar ratio between about 75:25 and 50:50.

Poly(lactide-co-glycolide) polymers preferably will range in molecular weight from about 20,000 to about 100,000, stated as an average. The molecular weight of a particular copolymer is independent of its monomeric makeup. For example, the preferred 50:50 copolymer can have a molecular weight which falls anywhere within this range. Therefore polymers can be varied both as to their monomer composition as well as their molecular weight and be within the scope and intent of this invention.

For the purposes of this invention the relative molecular weight of a particular polymer vis-a-vis a second polymer is stated in terms of its inherent viscosity in a particular solvent and at a particular temperature. The viscosity of a particular polymer is measured in a capillary viscometer using chloroform or haxafluoroisopropanol at 30° C. The results are stated in terms of deciliters/g (dl/g). There is a direct correlation between inherent viscosity and molecular weight.

A method for the preparation of polylactide polymers can be found in U.S. Pat. 3,773,919 and reference is made thereto for the preparation of the such polymers which is incorporated herein by reference.

Preparation of the microcapsules using any combination of the various peptides, polymer hydrolysis modifying agents or encapsulating polymer excipients noted above parallels the basic technique set out in U.S. Pat. 3,773,919. A full description of the procedure used herein can be found in that document.

In brief, the procedure involves dissolving the polymer in an halogenated hydrocarbon solvent, dispersing the aqueous polypeptide containing solution in this polymer-solvent solution, and adding some agent which is soluble in the halogenated hydrocarbon solvent but is a non-solvent for the encapsulating excipient. The addition of the non-solvent, called a coacervation agent, causes the polymeric excipient to precipitate out of the halogenated hydrocarbon solvent onto the dispersed polypeptide containing water droplets, thereby encapsulating the polypeptide. For example, a poly(lactide-co-glycolide) is dissolved in methylene chloride. An aqueous solution of polypeptide is then added with rapid stirring to the solvent-polymer solution forming a water-in-oil emulsion. A second solvent-miscible material such as a silicone oil, is added with slow stirring to cause the polymeric excipient to precipitate out of the methylene chloride and collect on the water-solvent interface which coats the dispersed water droplets to give microcapsules.

Halogenated organic solvents which may be used are most of the C1 to C4 halogenated alkanes such as, for example, methylene chloride, ethylene dichloride, ethylene chloride, 2,2,2-trichloroethane and the like.

Coacervation agents may be any solvent miscible polymeric, mineral oil or vegetable oil compounds which are non-solvents for the encapsulating polymers. There may be used, for example, silicone oil, peanut oil, soybean oil, corn oil, cotton seed oil, coconut oil, linseed oil, mineral oils and other related oils.

After being formed, the microcapsules are washed and hardened with a suitable organic solvent, washed with water, washed with an aqueous non-ionic surfactant solution, and then dried at room temperature under vacuum.

Microcapsules may range in diameter from about 1 to 500 microns, depending upon the techniques employed. For this invention it is preferred to have the microcapsule diameter be between 5 and 200 microns.

The prepared microcapsules may be administered to a subject by any means or route desired. However the most efficacious route is parenteral administration by injection, most preferably subcutaneously or intramuscularly.

If the capsules are to be administered by injection they may first be suspended in some non-toxic suspending vehicle. The exact make up of these injectable microcapsule suspensions will depend upon the amount of drug to be administered, the suspending capacity of the suspending agent and on the volume of solution which can be injected at a particular site or in a particular subject.

The compositions of this invention exhibit sustained release of the encapsulated compounds over extended periods of time. This time period may range from one month to 3 years depending on the composition of the encapsulating excipient, its molecular weight, the diameter of the capsule, and the presence of a polymer hydrolysis modifying agent in the core. Preferably the release time will be about 1 to 24 months.

SPECIFIC EMBODIMENTS OF THE INVENTION

The following examples illustrate the processes and compositions of this invention.

EXAMPLE I

This example describes the procedure for preparing a microcapsule composition wherein the polypeptide is (pyro)Glu-His-Trp-Ser-Tyr-3-(2-naphthyl)-D-alanyl-Leu-Arg-Pro-Gly-NH$_2$, (D-Nal(2)$^6$ LH-RH) present in an amount of 1.4% by weight, no polymer hydrolysis modifying agent is present, and the excipient is a 50:50 molar ratio poly(lactide-co-glycolide) copolymer having an inherent viscosity in hexafluoroisopropanol of 0.38 dl/g at 30° C.

Excipient, 4 g, was dissolved in 196 g of methylene chloride. This solution was placed in a 300 ml resin kettle equipped with a true-bore stirrer having a 2.5 inch Teflon turbine impeller driven by a Fisher "Stedi-Speed" motor. In a 1-dram glass vial was dissolved 0.0571 g of polypeptide in 1.34 g of deionized water.

This solution was added to the resin kettle During this addition, the dilute polymer solution was stirred at 3200 RPM to form a water-in-oil emulsion. With continued stirring at that rate, 80 ml of silicone oil was added at the rate of 4.0 ml/min by means of a peristaltic pump. The silicone oil caused the polymer to phase separate, and deposit as droplets of solvent-swollen polymer onto the surface of the water-polypeptide microdroplets. These solvent-swollen polymer droplets then coalesced to form a continuous film around the water-polypeptide microdroplets. The microcapsules were then hardened by pouring the contents of the resin kettle into a beaker containing 2000 ml of heptane. This mixture was stirred at 1000 RPM for 30 minutes with a stainless-steel impeller. The heptane-methylene chloride-silicone oil solution was removed by filtering the solution, employing a Buchner funnel and Whatman No. 41 filter paper. The microcapsules were then washed repeatedly with 100-ml aliquots of heptane to insure complete removal of the silicone oil. The microcapsules were then washed with deionized water followed by a wash with a 1% aqueous solution of Tween 20. and dried at room temperature under vacuum. Microcapsules obtained from this prepararion were determined to have diameters ranging in size from 10 to 40 microns.

The polypeptide containing microcapsules, whose preparation is described in the above paragragh, were suspended in a suspending vehicle and administered as a single subcutaneous injection to female Sprague-Dawley rats and female rhesus monkeys. The length of estrous suppression was calculated against the percentage of animals showing suppression.

The results of the monkey study are given in Table I below. Each data line represents one subject. The injected dose was as stated in the Table. Microcapsules were prepared as stated in Example I using that LH-RH analogue and a 50:50 molar ratio copolymer (PLA:PGA) having an inherent viscosity of 0.38 dl/g in hexafluoroisopropanol at 30° C. at a 1.4% peptide to polymer ratio. The microcapsule's diameter ranged from 10 to 40 microns.

TABLE I

EFFECT OF D-Nal(2)$^6$ LHRH RELEASED FROM PLA:PGA MICROSPHERES ON OVULATION IN RHESUS MONKEYS

| ANIMAL NO. | DOSE | INTERMENSTRUAL INTERVAL | | |
|---|---|---|---|---|
| | | BEFORE | DURING | AFTER TREATMENT |
| 1 | — | 25 | 30 | 28 |
| 2 | — | 28 | 27 | 26, 29 |
| 3 | 1 mg D-Nal(2)$^6$ | 30 | 67 | 27 |

TABLE I-continued

EFFECT OF D-Nal(2)$^6$ LHRH RELEASED FROM PLA:PGA MICROSPHERES ON OVULATION IN RHESUS MONKEYS

| ANIMAL NO. | DOSE | INTERMENSTRUAL INTERVAL | | |
|---|---|---|---|---|
| | | BEFORE | DURING | AFTER TREATMENT |
| 4 | 1 mg D-Nal(2)$^6$ | 24 | 83 | 27 |

A single 300 μg dose of D-Nal(2)$^6$ LH-RH microencapsulated at 1.4% peptide to polymer with a 50:50 molar ratio poly(lactide-co-glycolide) having a diameter ranging in size from 10–40 μm (inherent viscosity in hexafluoroisopropanol-0.38 dl/g) which had been suspended in a suspending agent (composition given in Example III) was injected subcutaneously in 10 mature female Sprague-Dawley rats. Estrous was determined by daily vaginal smear analysis. All rats showed estrous suppression through day 24 post dosing. At day 25, 40% showed estrous. By day 27 estrous was observed in all animals.

EXAMPLE II

Table II sets out several examples of polypeptide containing microcapsules wherein the following parameters were varied: lactide-glycolide mole ratio; molecular weight, stated as inherent viscosity; stir rate; addition rate of silicone oil; and the amount of silicone oil added. The polypeptide encapsulated here is the same as set out in Example I. The preparation techniques described in Example I were used to prepare these materials, except as note for the stirring rates and silicone oil addition rates.

TABLE II

| Batch | Excipient's Inherent Viscosity, dl/g | Lactide:Glycolide Mole Ratio | Polymer (g) | Peptide (g) | Silicone Oil | | | Capsule Size μm |
|---|---|---|---|---|---|---|---|---|
| | | | | | Am't Added (ml) | Rate Added (ml/min) | Stir Rate RPM | |
| A | 0.47$^2$ | 75:25 | 2.0 | 0.0266 | 40.0 | 2.0 | 1000 | 40.5% <45 44.4% >45 |
| B | 0.97$^2$ | 68:32 | 2.0 | 0.0255 | 40.0 | 4.0 | 3600 | 14.0% <45 77.0% >45 |
| C | 0.38$^1$ | 50:50 | 2.0 | 0.0263 | 40.0 | 4.0 | 3000 | 10–30 |
| D | 0.38$^1$ | 50:50 | 2.0 | 0.0279 | 40.0 | 4.4 | 3000 | 8–25 |
| E | 0.38$^1$ | 50:50 | 2.0 | 0.0297 | 135.0 | 2.0 | 1000 | 45–90 |
| F | 1.52$^1$ | 50:50 | 2.0 | 0.0253 | 40.0 | 4.0 | 3000 | 80–160 |

$^1$Inherent viscosity in hexafluoroisopropanol at 30° C.
$^2$Inherent viscosity in chloroform at 30° C.
In each of the above batches the following solvents and amounts are used:
to dissolve the peptide - 0.67 ml of deionized water;
encapsulation solution - 98 ml of methylene chloride.

EXAMPLE III

This example describes the encapsulation of bGH with 30% urea encapsulated in a polylactic/glycolic acid polymer having a molar ratio of 68/32 and an inherent viscocity of 0.8 dl/g. Specific quantities are set up below. These various materials were formulated into microcapsules in the same manner as described in Example I.

(1) Polymer: 68/32 polylactic/glycolic acid, of inherent viscosity 0.8 dl/g
Microspheres: 5% bovine growth hormone (bGH)
30% urea
65% polymer excipient
Manufacturing Parameters: Aqueous solution: BGH 308 mg
Urea 1.85 g
Water to 7.5 ml

|   |   |   |   |
|---|---|---|---|
| | | -continued | |
| | | pH 4.0 (adjusted with HCl) | |
| Organic | polymer excipient | | 4.0 g |
| solution: | methylene chloride | | 196.0 g |
| (2) Polymer: | 50/50 Polylactic/glycolic acid, of inherent viscosity 0.5 dl/g | | |
| Microspheres: | 10% bGH | | |
| | 30% Urea | | |
| | 60% Polymer excipient | | |
| Manufacturing | Aqueous solution: | bGH | 616 mg |
| Parameters: | | Urea | 1.85 g |
| | | Water to | 15.0 ml |
| | pH 4.0 (adjusted with HCl) | | |
| Organic | polymer excipient | | 4.0 g |
| solution: | methylene chloride | | 396.0 g |

EXAMPLE IV

The following describes a formulation for parenteral injection of polypeptide-containing microcapsules prepared according to the methods disclosed herein.

Microcapsules containing the LH-RH polypeptide (pyro)Glu-His-Trp-Ser-Tyr-3-(naphthyl)-D-alanyl-Leu-Arg-Pro-Gly-NH$_2$ in a concentration of 1.0% by weight and wherein the excipient polymer was poly(-lactide-co-glycolide) having a molar ratio of 50:50 and an inherent viscosity of 0.38 dl/g in hexafluoroisopropanol at 30° C. were suspended in the following solution:

Na CMC: 0 5%
NaCl: 0.8%
Benzyl alcohol: 0.9%
Tween 80: 0.1%
Purified water: q.s. 100%

For example, 330 mg of microcapsules were suspended in 5.5 ml to provide an injectable dose of 300 μg of peptide per 0.5 ml of injectable suspension.

The foregoing discussion and specific embodiments are intended to be exemplary as to the scope and practice of this invention and should not be read to limit the practice of the art described therein.

What is claimed is:

1. A pharmaceutical composition designed for sustained release of a luteinizing hormone-releasing hormone (LHRH) analog, prepared in microcapsule form, wherein the composition comprises at least one luteinizing hormone-releasing hormone analog or a pharmaceutically acceptable salt thereof in an amount between 0.01 and 40.0 weight percent, and a poly(lactide-co-glycolide) polymer having a molar ratio of 75:25 to 40:60, said polymer being present in an amount between 99.9 and 60 weight percent, which composition exhibits sustained release of an effective amount of the luteinizing hormone-releasing hormone analog over a period of at least one month.

2. The composition of claim 1 wherein said analog is an LHRH agonist.

3. The composition of claim 1 wherein said analog is an LHRH antagonist.

4. The composition of claim 2 wherein said analog is a nona-peptide or a decapeptide having the formula
(pyro)Glu-His-V-Ser-W-X-Y-Aro-Pro-Z and the pharmaceutically acceptable salts thereof wherein
V is tryptophyl, phenylalanyl or 3-(1-naphthyl)-L-alanyl;
W is tyrosyl, phenylalanyl or 3-(1-pentafluorophenyl)-L-alanyl;
X is a D-amino acid residue

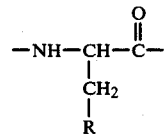

wherein R is
(a) a carbocyclic aryl-containing radical selected from the group consiting of naphthyl, anthryl, fluorenyl, phenylanthryl, biphenylyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;
Y is leucyl, isoleucyl, non-leucyl or N-methyl-leucyl;
Z is glycinamide or —NH—R$_1$, wherein
R$_1$ is lower alkyl, cycloalkyl, fluoro lower alkyl

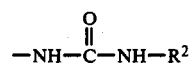

wherein R$_2$ is hydrogen or lower alkyl.

5. The composition of claim 4 wherein said analog is present in an amount between 0.1 to 10.0 weight percent.

6. The composition of claim 5 wherein said polymer has a molecular ratio of 75:25 to 50:50.

7. The composition of claim 6 in the form of injectable microcapsules.

8. The composition of claim 7 wherein the several substituents of formula I are defined as follows: said analog is defined:
V is tryptophyl or phenylalanyl;
W is tyrosyl;
X is 3-(2-naphthyl)-D-alanyl or 3-(2,3,6-trimethylphenyl)-D-alanyl;
Y is leucyl or N-methyl-leucyl; and
Z is glycinamide or NMEt; and said polymer has a molar ratio between 75:25 and 50:50.

9. The composition of claim 8 wherein said analog is (pyro)Glu-His-Trp-Ser-Tyr-3-(naphthyl)-D-alanyl-Leu-Arg-Pro-Gly-NH$_2$ and the pharmaceutically acceptable salts thereof.

10. The composition of claim 7 wherein said microcapsules are dispersed in a pharmaceutically acceptable carrier suitable for parenteral administration.

11. The composition of claim 1 wherein said LHRH analog has the formula (pyro) Glu-His-Trp-Ser-Tyr-D-Trp-Leu-Arg-Pro-Gly-NH$_2$ and the pharmaceutically acceptable salts thereof.

12. A composition according to claim 1, wherein the LHRH analog is an analog of natural LHRH, in which modification comprises the 6-position residue changed from Gly to a D-amino acid.

13. A composition according to claim 12, wherein the D-amino acid is D-Ala, D-Leu, D-Phe or D-Trp.

14. A composition according to claim 13, wherein the D-amino acid is D-Leu.

15. A composition according to claim 13, wherein the D-Amino acid is D-Trp.

16. A composition according to claim 12, wherein the 10-position is modified to afford a nona-peptide as an alkyl-, cycloalkyl- or fluoroalkyl amine.

17. A composition according to claim 12, wherein Gly-NH$_2$ is replaced by an β-azaglycine amide.

18. A composition according to claim 12, wherein N-methyl leucine is substituted for leucine in position 7.

* * * * *